(12) United States Patent
Jacquet et al.

(10) Patent No.: US 9,383,297 B2
(45) Date of Patent: Jul. 5, 2016

(54) DECALCIFICATION SOLUTION WITH PRESERVATION OF RNA

(71) Applicant: The University of Akron, Akron, OH (US)

(72) Inventors: Robin DiFeo Jacquet, Akron, OH (US); William Landis, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/934,779

(22) Filed: Jul. 3, 2013

(65) Prior Publication Data

US 2014/0011202 A1    Jan. 9, 2014

Related U.S. Application Data

(60) Provisional application No. 61/667,557, filed on Jul. 3, 2012.

(51) Int. Cl.
*G01N 1/30* (2006.01)
*C12Q 1/68* (2006.01)
*G01N 33/48* (2006.01)

(52) U.S. Cl.
CPC ............... *G01N 1/30* (2013.01); *C12Q 1/6806* (2013.01)

(58) Field of Classification Search
None
See application file for complete search history.

(56) References Cited

U.S. PATENT DOCUMENTS

| 6,204,375 | B1 | 3/2001 | Lader |
| 6,528,641 | B2 | 3/2003 | Lader |
| 8,178,296 | B2 | 5/2012 | Lader |
| 2012/0270316 | A1 | 10/2012 | Lader |

OTHER PUBLICATIONS

Mutter et al., "Comparison of frozen and RNALater solid tissue storage methods for use in RNA expression microarrays" 5 BMC Genomics 88 (2004).*

Baird et al., "A Technique of Decalcification Suited to Electron Microscopy of Tissues Closely Associated with Bone" 159 Anatomical Record 281-289 (1967).*
Walsh et al., "The effect of tissue decalcification on mRNA retention within bone for in-situ hybridization studies" International Journal of Experimental Pathology 237-241 (1993).*
Promega, "Recipes for Common Laboratory Solutions" Promega Technical Reference (2010).*
Shao, Yvonne Y., et al. "Analysis of gene expression in mineralized skeletal tissues by laser capture microdissection and RT-PCR," Laboratory Investigation (2006) v.86, pp. 1089-1095.
Van Meurs, J.B.J et al., "Quantification of mRNA levels in joint capsule and articular cartilage of murine knee joints by RT-PCR: kinetics of stromelysin and IL-1 mRNA levels during arthritis," Rheumatol Int., v.16, pp.197-205, 1997.
Shibata, Yasuaki, et al., "Assessment of decalcifying proticols for detection of specific RNA by non-radioactive in situ hybridization in calcified tissues," Histochem Cell Biol (2000) 113:153-159.
Kirviranta, I. et al., "The Rate of Calcium Extraction During EDTA Decalcification form Thin Bone Slices as Assessed with Atomic Absorption Spectrophotometry," Histochemistry v.68, pp. 119-127 (1980).
Brochure entitled "RNAlater® Tissue Collection: RNA Stabilization Solution" for Applied Biosystems (Ambion) Part Nos. AM7020, AM7024, AM7021, AM7022. (2010).
Ambion QC Form 0090 for "SUPERase•in(TM) RNase Inhibitor" (Catalog No. 2696) dated Sep. 8, 2004.
Callis, G. et al., "Decalcification of Bone: Literature Review and Practical Study of Various Decalcifying Agents, Methods, and Their Effects on Bone Histology," The Journal of Histotechnology vol. 21, No. 1, Mar. 1998 pp. 49-58.
Scharschmidt, T. et al., "Gene Expression in Slipped Capital Femoral Epiphysis" J. Bone Joint Surg Am. 2009;91:366-377.

* cited by examiner

*Primary Examiner* — Nancy J Leith
(74) *Attorney, Agent, or Firm* — Renner Kenner Greive Bobak Taylor & Weber

(57) ABSTRACT

The present invention is directed to methods of decalcification and tissue sample preparation that allows for the reproducible quantitative analysis of gene expression in hard tissue samples like bone, mineralizing cartilage and tendon, dentin, cementum and/or enamel that are too hard to section effectively using conventional means.

5 Claims, 9 Drawing Sheets

DECALCIFICATION SOLUTION WITH PRESERVATION OF RNA

CROSS REFERENCE TO RELATED APPLICATIONS

This application claims the benefit of U.S. provisional patent application Ser. No. 61/667,557 entitled "Decalcification Solution with Preservation of RNA," filed Jul. 3, 2012, and incorporated by reference in its entirety.

FIELD OF THE INVENTION

The present invention is in the field of molecular biology and more specifically the preparation of bone or other hard tissue samples for gene expression analysis and/or other analyses where RNA preservation is important.

BACKGROUND OF THE INVENTION

In scientific research studies in the general area of cell biology, investigations of both soft and hard (mineralized) tissues are commonplace. Examination and analysis of hard tissues such as bones and teeth, the shells of mollusks and other examples of vertebrate, invertebrate, plant, bacterial and other organisms often encounter difficulties since these tissues in many instances must be specially treated to remove their constituent mineral. For investigations to determine nucleic acids, genes, and proteins of both soft and hard tissue cells, a frequent method of processing involves cutting the cells into very thin sections. Again, the demineralization of the hard tissues is required for proper and consistent sectioning.

Decalcification can be accomplished by utilizing any of several different methodologies, including application of chelating reagents, acids or even microwave radiation. There are many products currently on the market and available for demineralization, intended to assist in hard tissue treatment for routine clinical and basic science research in the field of protein analysis.

For aspects of cell biology concerning nucleic acid, and particularly ribonucleic acid (RNA), research and gene studies, additional techniques must be carefully considered. Because gene expression can change within seconds of cell processing, tissues must be handled in a way that does not change or degrade (destroy) the cellular RNA. In the cases of human, animal or plant tissues, RNA analysis had generally required that the samples be snap-frozen in liquid nitrogen at the immediate point of their retrieval upon death or surgical removal. Snap-frozen RNA has proven to be of the highest quality and other methods are usually compared to this standard.

More recently, however, RNA preservation solutions like RNALATER™ Solution have been developed to stabilize RNA in animal, human or other tissues without the need for snap freezing. It has been found that, samples stored in RNALATER™ Solution were of a quality comparable to samples processed and stored following snap-freezing. This was a significant advance in nucleic acid preservation, since it was often impossible, especially away from the laboratory and out in the field, to have access to or carry the liquid nitrogen necessary for snap freezing.

The importance of RNA preservation has continued to grow with the development of more and more sophisticated genetic analyses using various types of RNA. In particular, researchers and medical professionals have been utilizing gene expression analysis to both diagnose and treat various maladies and for basic scientific research. While each cell in an organism will contain the same genomic DNA and accordingly the same "genes," only a small fraction of the genes in any particular cell or cell type is ever used at any one time. When a particular gene is activated, the genetic information necessary to create the prescribed protein is transcribed to the ribonucleic acid (RNA) that will be used to make the desired protein.

By identifying and quantifying the RNA in a sample, gene expression analysis makes it possible to determine both what genes are being expressed and, often more importantly, when, where, and in what concentration those genes are being expressed. That is, if the location from which the RNA was recovered can be accurately determined, then the particular cells or cell types that are responsible for the gene expression can likewise be determined. The location of the cells or cell types studied, and, therefore the source of the RNA recovered from the sample, is ordinarily a matter of careful sectioning of the sample to be tested. From the sample section, specific cells, cell types etc. can be selected for analysis using techniques such as manual or laser capture microdissection. Two increasingly common types of gene expression analyses are In-Situ Hybridization (ISH) and laser capture microdissection (LCM).

ISH analysis of RNA requires sections to be cut from chemically fixed tissue samples and then molecular probes are used to label and identify genes of interest in these sections. RNA may be visualized by the labeling in particular areas of the sections and analyzed qualitatively in a temporospatial manner. The detection of labeled genes in hard tissues again requires demineralization to achieve optimal results.

LCM methodology is unique compared to other procedures for gene (and protein) identification in that specific cells of interest, identified by viewing them under a microscope within a population of cells, may be precisely removed from a tissue section using a laser beam. The isolated and so-called captured cells may then be analyzed to address a multitude of questions dealing with gender, disease, drug and other effects on a specimen. RNA obtained following LCM capture of one or several cells in sections may subsequently be assessed quantitatively using reverse transcription-quantitative polymerase chain reaction (RT-qPCR) analysis. Resulting data offer insight into biochemical reactions and pathways in a more direct manner than that of ISH. LCM is a microscopic technique requiring tissues to be sectioned onto particular slides of either glass or a thin polymer membrane. Hard tissue study by LCM normally requires demineralization of the sample.

A common approach to analyze specific cell types, individually or as groups of cells spatially, is cryosectioning. Samples are snap-frozen and embedded in a tissue freezing medium available commercially. The frozen tissue or biopsy is sectioned into 4-20 µm slices in a cryostat instrument and kept frozen to preserve the RNA until isolation and analysis. This routine procedure for analysis is easily accomplished on tissues that are by nature soft, i.e., kidney or liver. This approach does make it possible to determine with some precision what cells and cell types are being analyzed.

Analysis of hard tissues like bone, mineralizing cartilage and tendon, dentin, cementum, and enamel, as well as invertebrate shells and other tissues which are too hard to cut or section effectively using conventional means, such as a cryostat has been found, however, to be a major problem. There have developed a variety of approaches to preparing these types of hard tissues for gene expression analysis. One common approach is to snap-freeze and then grind the hard tissue into a powder, and extract the RNA for analysis. While this approach does produce RNA for gene expression analysis relatively quickly without significant degradation, the gene data obtained using this method relate to all of the cells present in the sample. Because of this, it is not possible to determine what specific phenotype or lineage in population of cells/cell types present in the typically mixed cell groupings are producing the RNA obtained.

Another approach is to decalcify the hard tissue sample with acids or chelating agents, thereby softening it so it can be cryosectioned and analyzed. The two most common groups of decalcifying agents known in the art are chelating agents and acids. The acids may be further divided into weak organic (picric, acetic and formic acid) and strong inorganic acids (nitric and hydrochloric acid). The acids dissolve hydroxyapatite mineral with release of calcium ions while chelating agents take up or capture the calcium ions within their structure. The most frequently clinically used chelating agent is ethylenediaminetetraacetic acid (EDTA).

Unfortunately, however, RNA is relatively fragile and tends to break down rapidly after the tissue sample is taken and known decalcification agents have been found to degrade the RNA in the sample. Acids used for decalcification in other procedures are very harsh, and with chelating agents such as EDTA or disodium-EDTA, the decalcification process can take as long as four to six weeks. The RNA recovered using this process is often degraded to the point that it can not be quantitated in any reliable manner. While increasing the concentration of the decalcification agent has been found to speed decalcification, it also increases the rate of degradation of the RNA in the sample.

Accordingly, there is a need in the art for a method for the rapid decalcification of hard tissues like bone, mineralizing cartilage and tendon, dentin, cementum and other tissues that are too hard to section effectively using conventional means, which preserves the ability to determine the site of gene expression without significantly degrading the RNA recovered for analysis.

SUMMARY OF THE INVENTION

The present invention is directed to a method of decalcification that allows the reproducible quantitative analysis of gene expression for hard tissue samples like bone, mineralizing cartilage and tendon, dentin, cementum and other tissues that are too hard to section effectively using conventional means.

In one aspect, the present invention is directed to a method of preparing a decalcification agent solution for the decalcification of hard tissues like bone, mineralizing cartilage and tendon, dentin, cementum and enamel without degrading the ribonucleic acids (RNA) contained therein, comprising the steps of: providing an RNA preservation solution; adding a decalcification agent to said RNA preservation solution; wherein said decalcification agent further comprises tetrasodium-ethylenediaminetetra-acetic acid (tetrasodium-EDTA) or trisodium-ethylenediaminetetra-acetic acid (trisodium-EDTA); adjusting the pH of the mixture to a pH of from about 8 to about 10 and stirring until the decalcification agent is substantially dissolved; readjusting the pH of the mixture to a pH of from about 7.2 to about 7.7; and sterilizing and collecting the mixture in a sterilized container.

In some embodiments of the present invention, the decalcification agent is tetrasodium-ethylenediaminetetra-acetic acid (tetrasodium-EDTA). In some embodiments, the method of the present invention may include any of the embodiments described above wherein the mixture is stirred for from about 30 minutes to about 60 minutes. In some embodiments, the method of the present invention may include any of the embodiments described above wherein the pH of the mixture is adjusted to a pH of about 7.4.

In some embodiments, the method of the present invention may include any of the embodiments described above wherein the mixture is sterilized by filtration. In some embodiments, the method of the present invention may include any of the embodiments described above wherein the mixture is sterilized using a 0.2 µm filter.

In another aspect, the present invention is directed to a method of decalcification of hard tissues like bone, mineralizing cartilage and tendon, dentin, cementum, enamel and other examples for sectioning without degrading the ribonucleic acids (RNA) contained therein, comprising the steps of: obtaining a hard tissue sample and placing it in an RNA preservation solution; removing said hard tissue sample from the RNA preservation solution and placing it in a liquid decalcification medium comprising an RNA preservation solution and a decalcification agent, wherein said decalcification agent is selected from the group consisting of tetrasodium-EDTA or trisodium-EDTA wherein said decalcification agent begins to remove calcium from mineral deposits in said hard tissue sample; stirring the mixture said until said hard tissue sample softens for sectioning; and rinsing the softened hard tissue sample in an RNA preservation solution to remove any remaining decalcification agent.

In some embodiments, the method of the present invention may include any of the embodiments described above wherein said hard tissue sample is a tissue sample selected from the group consisting of bone, mineralizing cartilage and tendon, dentin, cementum, enamel and others. In some embodiments, the method of the present invention may include any of the embodiments described above wherein the size of said hard tissue sample does not exceed 0.5 cm, on one side.

In some embodiments, the method of the present invention may include any of the embodiments described above wherein said hard tissue sample is placed in said RNA preservation solution for a period of from about 18 hours to about 24 hours at a temperature of from about 3° C. to about 4° C. In some embodiments, the method of the present invention may include any of the embodiments described above wherein said hard tissue sample is placed in said RNA preservation solution for about 1 day at a temperature of about 4° C. In some embodiments, the method of the present invention may include any of the embodiments described above wherein said decalcification agent is tetrasodium-ethylenediaminetetra-acetic acid (tetrasodium-EDTA).

In some embodiments, the method of the present invention may include any of the embodiments described above wherein the ratio of the volume of said decalcification agent to the weight of said hard tissue sample is from about 10:1 to about 20:1. In some embodiments, the method of the present invention may include any of the embodiments described above wherein the mixture is stirred for from about 3 days to about 7 days. In some embodiments, the method of the present invention may include any of the embodiments described above wherein the liquid decalcification medium is changed from every about 36 to every about 48 hours. In some embodiments, the method of the present invention may include any of the embodiments described above wherein the decalcification agent is removed from said tissue sample by rinsing said tissue sample in an RNA preservation solution for a period of time from about 12 hours to about 24 hours. In some embodiments, the method of the present invention may include any of the embodiments described above further comprising the step of: rinsing the tissue sample in RNase-free water to remove any remaining RNA preservation solution.

In another aspect, the present invention is directed to a method of preparing hard tissues like bone, mineralizing cartilage and tendon, dentin, cementum, enamel and other examples for gene expression analysis comprising the steps of: obtaining a hard tissue sample; trimming said hard tissue sample to a minimum size needed for gene expression analysis, wherein said tissue sample has at least one edge that is less than 0.5 cm in length; placing said hard tissue sample in an RNA preservation solution; removing said hard tissue sample from the RNA preservation solution and placing it in a liquid decalcification medium comprising a decalcification agent selected from the group consisting of tetrasodium-EDTA or trisodium-EDTA and an RNA preservation solution, wherein said decalcification agent begins to remove calcium from mineral deposits in said hard tissue sample, causing said hard tissue sample to soften; stirring the mixture until enough of the calcium has been removed from the mineral deposits in said hard tissue sample to cause the tissue sample to soften enough to permit sectioning of said tissue sample; rinsing the softened hard tissue sample in RNA preservation solution and then RNase-free water; soaking the softened hard tissue sample in cryoembedding medium for from about 45 minutes to about 60 minutes; freezing the infiltrated sample and cryo-sectioning the softened hard tissue sample.

In some embodiments, the method of the present invention may include any of the embodiments described above wherein said hard tissue sample is a tissue sample selected from the group consisting of bone, mineralizing cartilage and tendon, dentin, cementum, the shells of mollusks, and other mineralized tissue of vertebrate, invertebrate, plant, bacterial and other organisms. In some embodiments, the method of the present invention may include any of the embodiments described above wherein said decalcification agent is tetrasodium-EDTA. In some embodiments, the method of the present invention may include any of the embodiments described above wherein the ratio of the volume of said decalcification agent to the approximate weight of said hard tissue sample is from about 10:1 to about 20:1.

In some embodiments, the method of the present invention may include any of the embodiments described above wherein the mixture is stirred for from about 3 days to about 7 days. In some embodiments, the method of the present invention may include any of the embodiments described above wherein the decalcification agent added is changed from every about 36 to every about 48 hours.

In some embodiments, the method of the present invention may include any of the embodiments described above further comprising the step of adding a ribonuclease inhibitor to the liquid decalcification medium to prevent degradation of the RNA in said hard tissue sample. In some embodiments, the method of the present invention may include any of the embodiments described above wherein said method of preparing further includes the steps of: removing cells from the sectioned tissue sample of using a laser; and extracting the RNA from said cells and analyzing said RNA for gene expression.

In another aspect, the present invention is directed to a kit for preparing hard tissue samples for gene expression analysis using the method of any of the embodiments described above. In some embodiments, the kit of the present invention may include any of the embodiments described above, further comprising a first container containing an RNA preservation solution; a second container containing a decalcification agent solution; and a written protocol for using said solutions to prepare a hard tissue sample for later gene expression analysis. In some embodiments, the kit of the present invention may include any of the embodiments described above, wherein said decalcification agent solution further comprises tetrasodium-EDTA. In some embodiments, the kit of the present invention may include any of the embodiments described above, wherein said first container further comprises a ribonuclease inhibitor to prevent degradation of the RNA in the tissue sample.

BRIEF DESCRIPTION OF THE DRAWINGS

For a more complete understanding of the features and advantages of the present invention, reference is now made to the detailed description of the invention along with the accompanying figures in which:

FIG. 5A was taken before LCM to show the intact section.

FIG. 11A was taken before LCM to show the intact section.

DETAILED DESCRIPTION OF THE ILLUSTRATIVE EMBODIMENTS

Figure 1:
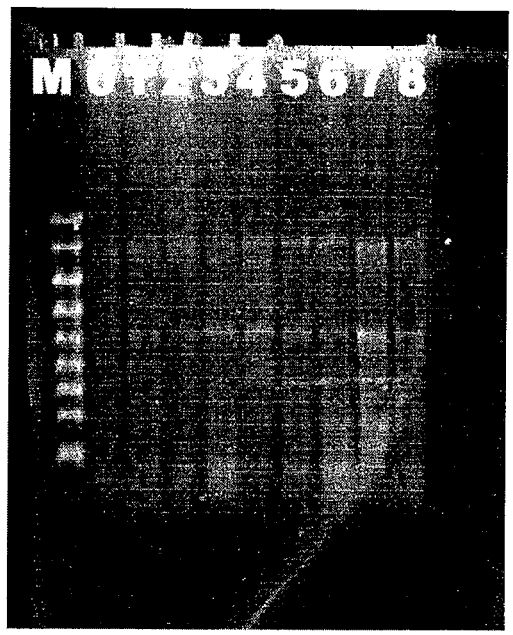
FIG. 1 is a scanned image of 1% formaldehyde denaturing agarose gel. A size marker was run in the first lane followed by RNA isolated from rat bones ground to powders under liquid nitrogen. Day 0 (0) was the control and was not immersed in decalcification solution. Subsequent lane numbers refer to days rat bones were being demineralized in decalcification solution. RNA was observed to be intact across all time points and 28S and 18S r RNA bands were observed.

The present invention is directed to a method of decalcification that allows for the reproducible quantitative analysis of gene expression in hard tissue samples like bone, mineralizing cartilage and tendon, dentin, cementum, enamel and/or other tissues or organisms that are too hard to section effectively using conventional means.

In some embodiments of the method the present invention, a tissue sample containing a hard tissue is taken from a human, animal or plant subject being studied. The human or animal tissue sample may be obtained surgically by any conventional means including by biopsy or by removal after death. As used herein, the term "hard tissue" refers to any mineralized tissue including, but not limited to, bone, mineralizing cartilage and tendon, dentin, cementum, enamel, the shells of mollusks, and any other tissue of vertebrate, invertebrate, plant, bacterial and/or other organisms that is sufficiently mineralized to be difficult or impossible to cut into useful sections for analysis using conventional means, including but not limited to, a cryostat. The tissue sample should be thin enough in at least one dimension to permit the decalcification agent solution (discussed below) to fully infiltrate the sample. As will be appreciated by those of ordinary skill in the art, the size and shape of sample which can be decalcified will also depend on the type of sample, its location and function. Some samples contain more mineral and may be more or less compact (cancellous and cortical bone for instance). In some embodiments, the tissue sample may be a sample of bone less than 5 mm, on any one side. In some embodiments, the tissue sample may be cut down to a size that will permit the decalcification agent solution to fully infiltrate the sample.

Being a single-stranded nucleic acid, RNA is relatively fragile compared to the double-stranded deoxyribonucleic acids (DNA) and has a relatively transitory and/or temporary existence in the cell. Moreover, it is known that upon cell death, enzymes are released to begin breaking down RNA. So, while it is not required to practice the present invention, it is strongly suggested that the tissue sample be placed in an RNA preservation solution as soon as possible after it is taken in order to prevent, or at least delay, the breakdown of the RNA in the sample. Suitable RNA preservation solutions are commercially available and include, for example, RNALATER™ Solution made by Ambion, Inc. (Carlsbad, Calif.), but may be any medium that prevents or delays degradation of RNA. The RNA preservation solution should be used according to its instructions with RNase-free conditions for the tissue sample being harvested. The amount of RNA preservation solution used will, of course, depend upon the particular solution chosen, but in some embodiments the volume of RNA preservation solution may be about 10 times the volume-to-weight of the tissue sample. In some embodiments, tissue samples may be placed in RNALATER™ Solution at 4° C. after being taken from the subject. In some embodiments, tissue samples may be immediately frozen after being taken from the subject. In some embodiments, tissue samples may be taken from bones, teeth, joints, tendons, ligaments or other examples.

The tissue sample can be kept in the RNA preservation solution for any period of time consistent with the written instructions and protocols for the RNA preservation solution provided by the manufacturer. In some embodiments, the tissue sample is placed in the RNA preservation solution for a period from about 18 hours to about 24 hours at a temperature from about 3° C. to about 4° C., prior to decalcification. In some embodiments, the tissue sample is placed in the RNA preservation solution for about 1 day at a temperature of about 4° C.

The decalcification solution may be prepared by adding a decalcification agent to an RNA preservation solution. The decalcification agent may be a chelating agent. The decalcification agent must be capable of reacting with and removing minerals, primarily calcium, found in the tissue sample without significantly damaging the surrounding tissues and must do so relatively quickly in order to limit the degradation of the RNA in the sample. Suitable decalcification agents include, but are not limited to, tetrasodium-ethylenediaminetetra-acetic acid (tetrasodium-EDTA) and trisodium-ethylenediaminetetra-acetic acid (trisodium-EDTA), and salts thereof. In some embodiments, the decalcification agent may be tetrasodium-EDTA. The concentration of decalcification agent in the decalcification solution will depend, of course, on the particular chelating agent being used but is ordinarily from about 9 to about 10 grams of decalcification agent per every 90 ml of RNA preservation solution. In some embodiments, the ratio of tetrasodium-EDTA salt (g) to RNA preservation solution (ml) is about 1:10.

The decalcification agent should also be either soluble in the RNA preservation solution or, to the extent not soluble, capable of forming a substantially stable and homogeneous mixture with the RNA preservation solution. In some embodiments, the pH of the RNA preservation solution and chelating agent mixture is increased to a pH of from about 8 to about 10 and stirred for from about 15 minutes to about 30 minutes until the decalcification agent is fully dissolved in the RNA preservation solution. In some embodiments, the pH of the RNA preservation solution and chelating agent mixture/solution is adjusted by the dropwise addition of a base. In some embodiments, the pH of the RNA preservation solution and decalcification agent mixture/solution is adjusted to a pH of from about 8 to about 9 to permit the decalcification agent to dissolve. In some embodiments, the RNA preservation solution and decalcification agent mixture/solution are stirred for from about 30 minutes to about 60 minutes to permit the decalcification agent to dissolve. In some embodiments, the RNA preservation solution and decalcification agent mixture/solution are stirred for approximately 30 minutes to permit the decalcification agent to dissolve.

Once the decalcification agent has dissolved in the RNA preservation solution, the pH of the solution is then readjusted to be a pH of between from about 7.2 to about 7.7, by any suitable means. In some embodiments, the pH of the solution is readjusted to be a pH of between from about 7.2 to about 7.4. In some embodiments, the pH of the solution is readjusted to be a pH of about 7.4. In some embodiments, the pH of the solution is readjusted to be a pH of about 7.6. In some embodiments, the pH of the solution is readjusted by the dropwise addition of 6N HCl.

As will be appreciated by those of skill in the art, the RNA in human cells and more vascularized animal and plant cells is particularly sensitive and prone to degradation. When working with these types of cells, a ribonuclease inhibitor may be added to the decalcification solution to further prevent, or at least limit, degradation of the RNA in these more sensitive samples. Many suitable ribonuclease inhibitors are commercially available and include, but are not limited to SUPERASE●IN™ (Ambion, Inc., Carlsbad, Calif.). In some embodiments, the concentration of ribonuclease inhibitor in the decalcification solution may be from about 30 U/ml to about 60 U/ml. In some embodiments, the concentration of the ribonuclease inhibitor in the decalcification solution is about 50 U/ml.

As will be appreciated by those of skill in the art, the decalcification solution must be sterilized before it can be used. Sterilization may be performed by any suitable method known in the art, but it is preferably done by filtration through a filter having a pore size fine enough to remove bacteria and other microbes and into a suitable sterile container. In some embodiments, the filter has a pore size of from about 0.4 μm to remove large particles and then less than 0.2 μm for sterilization. In some embodiments, the decalcification solution is sterilized by passing it through a 0.2 μm filter and into a suitable sterile container.

To begin decalcification, the tissue sample is immersed in an excess of decalcification solution prepared as set forth above. In some embodiments, the ratio of the volume of the decalcification solution to the approximate weight of the hard tissue sample is from about 10:1 to about 20:1. In some embodiments, the ratio of the volume of the decalcification solution to the approximate weight of the hard tissue sample is about 20:1.

The tissue sample is kept in the decalcification solution for from about 3 days to about 8 days depending upon the concentration of the decalcification agent and the size and relative mineral content of the sample, until the sample has softened to the point that it can be sectioned by conventional techniques. In some embodiments, the decalcification solution containing the tissue sample may be stirred. In some embodiments, the decalcification solution may be stirred for from about 3 days to about 7 days. In some embodiments, the sample is placed in the decalcification agent solution for 5 days.

The decalcification/chelating agent in the decalcification solution chemically reacts with the mineral deposits, binding primarily calcium, reducing the crystal size and thereby solubilizing the mineral. There can be other metals in bone and other hard tissue but the main purpose for a chelating agent like tetrasodium-EDTA in this application is to remove the calcium from the hydroxyapatite, thereby leaving phosphate ions in solution which have no calcium with which to bind and will bind with the available sodium in the tetrasodium-EDTA.

The solubilizing of the hydroxyapatite calcium phosphate crystals weakens or softens the hard tissue. It is believed that chelating agents like tetrasodium-EDTA work by capturing metallic ions like calcium from the external layer of the apatite crystals within their structure, removing them from the hydroxyapatite crystals. When all of the calcium ions from the outer layer of hydroxyapatite crystals have been captured, they are replaced by calcium ions from deeper layers. In this way, the crystal size decreases gradually, producing an excellent gradual decalcification of tissue components. This gradual decalcification produces an excellent means of maintaining tissue structure during decalcification and thereby excellent preservation of tissue components.

It also should be appreciated, however, that after some time the reaction will reach equilibrium and it may be necessary to periodically change the decalcification solution. In some embodiments, the decalcification solution may be changed at intervals of from about 36 hours to about 48 hours. In some embodiments, the decalcification solution is changed every 48 hours.

As set forth above, the sample should be kept in the decalcification solution until it becomes softened to the point that it can be sectioned by conventional techniques. However, it should be appreciated that the tissue sample need not be decalcified beyond the point necessary to work with and/or section it. While it is believed that tetrasodium-EDTA and trisodium-EDTA are better than the decalcification agents in the prior art, extended exposure to these chelating agents will gradually begin to degrade the RNA in the sample, and to the extent possible should be avoided. Extensive over-decalcification can destroy nucleic acids and proteins and results in poor sections where the tissue falls apart upon cutting with loss of morphological characteristics necessary for analysis.

The softened tissue sample is then rinsed first in RNA preservation solution and then in RNase-free or DEPC-treated water at a temperature of from about 3° C. to about 4° C. The softened tissue sample is then immersed in a small beaker containing a commercially available cryo-embedding medium for infiltration into the porous tissue that will result in more intact sections. Suitable commercially available cryo-embedding medium are known to those of skill in the art and may include, but are not limited to, Cryo-OTC (Andwin Scientific, Schaumburg, Ill.) and Tissue Freezing Media (TFM™) (Triangle Biomedical Sciences, Inc., Durham, N.C.). Typically, 45-60 min at a temperature of from about 3° C. to about 4° C. will be necessary before the sample is snap-frozen at minus 20° C. in a cryostat in preparation for sectioning.

Methods for analyzing specific cell types in heterogeneous tissue samples have long been pursued with the microdissection of certain cell populations accomplished in the past by a skilled scientist and a scalpel. The technology of the present time utilizes automated instruments with lasers that are capable of dissecting out specific cells, cell types or populations of cells (such as diseased from healthy) from a tissue for downstream genomic and proteomic analyses. Laser microdissection requires the tissue to be sectioned and most often stained for viewing and identifying populations of cells of interest to be microdissected and analyzed. Because this methodology can only be utilized on sectioned material, this invention allows for the analysis of such hard tissues that cannot be cut without decalcification. Decalcification can be accomplished by other products for such applications that involve protein and possibly DNA analysis but there is not a methodology and solution available for consistent, reliable gene expression (RNA) analysis. Laser microdissection provides the investigator with quantitative differences in downstream reverse transcription quantitative polymerase chain reaction (RT-qPCR) analyses.

This invention can also be utilized and is extremely beneficial for studies involving in situ hybridization. Similar to laser microdissection, in situ hybridization requires sections of the tissue of interest to visualize the location of cell types in a heterogeneous sample. Unlike microdissection, cells are not removed from the tissue, but the RNA or gene of interest is identified by binding a labeled chromogenic or fluorescent probe to the section. In this way, RNA expression can be microscopically identified and determined for specific areas or cell types. Although not a quantitative methodology per se, localization of the gene expression of molecules of interest can provide a spatial map of events in the tissue. This methodology has been used in conjunction with laser microdissection in gene expression analysis studies. This invention provides tissue sections of hard material that are decalcified to retain the RNA intact for in situ probes to bind.

It has, moreover, been found that the decalcification process of the present invention provides RNA comparable in quality and quantity to that provided by the snap-freezing the sample in liquid nitrogen and grinding it to a powder, which is considered the gold standard in the art for RNA recovery from hard tissues. But unlike that method, the present method also makes it possible to determine the location in the sample from which the RNA was recovered.

In another aspect, the present invention is directed to a kit for use in the preparation of hard tissues according to the methods described above. It is envisioned that the kit will comprise a container holding an appropriate volume of RNA preservation solution, a container holding an appropriate volume of decalcification solution as described above, and a written protocol for using the solutions to prepare a hard tissue sample for later gene expression analysis according to the method set forth above. In some embodiments, the decalcification solution may contain tetrasodium-EDTA and the chelating and decalcification agent.

In light of the foregoing, it should be appreciated that the present invention significantly advances the art by providing a method of decalcification that allows the reproducible quantitative analysis of gene expression for hard tissue samples that is an improvement over the prior art methods in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of the examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is average molecular weight, temperature is in degrees Centigrade, and pressure is at or near atmospheric.

Example 1

Synthesis of a Standard 50 ml Decalcification Solution According to One Embodiment of the Present Invention 40 ml of RNALATER™ was measured into a 100 ml baked beaker (RNase-free) at room temperature. 5 g tetrasodium-EDTA (ethylenediaminetetra-acetic acid) salt was then added as a decalcification agent. The solution pH was then adjusted to be above 8.0 by drop wise addition of 10% NaOH. The solution was stirred for about 30 minutes, until all of the tetrasodium-EDTA salt had dissolved. The solution volume was then adjusted to 50 ml with additional RNALATER™ and the pH readjusted to 7.6 by dropwise addition of 6N HCl. The total solution was then sterilized by passing it through a 0.2 μm filter into a sterile conical tube.

Example 2

Analysis of RNA Integrity after Decalcification of Mouse Bone Samples for Sectioning within a Short Time Frame First, 5G of ethylenediamine tetraacetic acid as a tetrasodium salt was placed in 40 ml of RNALATER™ Solution (Ambion, Life Technologies). When the tetrasodium-EDTA did not initially dissolve, the pH was increased to above 8.0 by the addition of sodium hydroxide (10N) with stirring for 30-60 min. After dissolution, the pH was decreased to 7.6 with acid (6N HCL). The solution volume was adjusted to a final volume of 50 ml with RNALATER™ Solution. The homogenous mixture was sterile filtered through a 0.2 μm filter in preparation for use. This solution was used in an initial experiment to determine time frame of the process of decalcification in relation to RNA degradation and feasibility of its use at 10% tetrasodium-EDTA concentration.

Second, sixteen mouse tibial bones (left and right rear sides), 1.6-1.9 cm in length and less than 5 mm in diameter, were harvested from eight black mice (CD-1) that were 8-10 months old. Two bones were flash frozen in liquid nitrogen and stored at minus 80° C. (day 0). The remaining 14 bones were placed in RNALATER™ Solution for approximately 24 hrs at 4° C. After 24 hrs, the bones were divided into two beakers (right and left sides) containing 10 ml of decalcification solution made as set forth above. Mouse tibial bones weigh 75-100 mg each and approximately 700 mg or 7 bones is equivalent to 7 ml of decalcification solution (10×). Decalcification solution was changed on days 2, 3, 6 and 8.

Third, two mouse bones, one from left side beaker and one from right side beaker, were removed from the decalcification solution at 7 time points, 24 hrs, 2, 3, 6, 7, 8, and 9 days. Upon removal, they were flash frozen in liquid nitrogen and stored at minus 80° C. All samples were analyzed for RNA quality and quantity and compared to day 0.

The mouse bones began to soften by day 3 and by day 9 were malleable. RNA quality and quantity decreased by day 9 according to UV 260/280 ratios.

Fourth, four additional mice tibias were harvested and placed in RNALATER™ Solution at 8:30 am at 4° C. Five grams of tetrasodium-EDTA was added to a 100 ml beaker containing 40 ml of RNALATER™ Solution. pH was adjusted to 9 with 10N NaOH and stirred for 45 min to dissolve the tetrasodium-EDTA. pH was reduced to 7.6 with acid and volume adjusted to 50 ml with RNALATER™ Solution. At 5 pm, 20 ml of cold decalcification solution was added to the 4 mouse bones and stirred. After 40 hrs, the first mouse tibia was removed and allowed to rinse in RNALATER™ Solution for 8 hrs. The bone was embedded in tissue freezing media in a cryostat (−20° C.) and sectioning was attempted but the bone was still too difficult to cut. Another tibia was removed at 48 hrs and placed in RNALATER™ Solution to rinse overnight and the decalcification solution (15 ml) was changed. The final two bones were subsequently removed from decalcification solution at 72 and 96 hrs with decalcification solution (15 ml) changed again after 72 hrs. The final solution at 96 hrs was tested with ammonium oxalate for completeness of demineralization and found to be complete.

Last, the remaining three decalcified bones from subsequent days were embedded in tissue freezing in a cryostat (−20° C.) and sectioning was accomplished without difficulty. This example showed small compact bone (1.6-1.9 cm by 3-4 mm) could be sectioned after 48 hrs without difficulty with this invention and over decalcification could lead to loss of RNA quantity and quality.

Example 3

Analysis of RNA Integrity after Decalcification of Rat Bone Samples for Sectioning within a Short Time Frame First, 10.0 grams of tetrasodium-EDTA was weighed out into a 150 ml sterile beaker and 80 ml of RNALATER™ Solution was added. The pH of the mixture was adjusted to 8.8 and the tetrasodium-EDTA was dissolved with stirring. The pH was then reduced to 7.6 and RNALATER™ Solution was added to an adjusted final volume to 100 ml. The solution was sterilized by passing it through a 0.2 μm filter and into a sterile container for subsequent use. The solution was stored at 4° C.

Second, the right and left tibias were removed from 5 adult rats. The tibias weighed approximately 1 gram and were 3 cm long by 0.5 cm in diameter. All 10 tibias were placed in RNALATER™ Solution for approximately 24 hrs at 4° C. After 24 hrs, one tibia was removed and flash frozen in liquid nitrogen and stored at minus 80° C. (day 0). Remaining 9 bones were placed in 100 ml of decalcification solution with slow, constant stirring at 4° C.

Third, one tibia each was removed after decalcification for 1, 2, 3, 4, 5, 6, and 7 days with two remaining bones removed after day 8. Each bone was immediately flash frozen in liquid nitrogen upon removal and stored at minus 80° C. Decalcification solution was only changed on days 3 and 6. On day 3, the bone would not indent with pressure from a blunt metal point of a forceps. On day 4, 10 ml of decalcification solution was removed and checked for completeness of demineralization with 5% ammonium oxaloacetate but a precipitate formed indicating the bones were only partial decalcified. By day 5, the rat bone was indenting or softening when touched with the forceps but just close to cartilaginous endplates. On day 6, the thick cortical midshaft was still hard with little deformation from forceps. By day 8, remaining rat bones were removed since there appeared to be no change from previous 2 days.

Last, RNA was extracted from all collected bones ground to powder and analyzed by a 1% formaldehyde agarose gel. See FIG. 1. A size marker was run in the first lane followed by RNA isolated from rat bones ground to powders under liquid nitrogen (gold standard) on subsequent days starting with day 0. Days indicate the amount of time the bone was immersed in decalcification solution. RNA was intact across all time points by 28S and 18S rRNA bands observed in all lanes. FIG. 1. It was concluded that mouse and even thicker rat bones can be decalcified using the method set forth above in a time frame where they can be sectioned and RNA quality is maintained.

Example 4

Quantitative Analysis of Gene Expression of Bones Bisected where Half are not Decalcified and the Other Half Decalcified in New Decalcification Solution First, 10.0 grams of tetrasodium-EDTA was weighed out into a 150 ml sterile beaker and 80 ml of RNALATER™ Solution was added. The pH of the mixture was adjusted to 9 and the tetrasodium-EDTA was dissolved with stirring. The pH was then reduced to 7.6 and RNALATER™ Solution was added to an adjusted final volume to 100 ml. The solution was sterilized by passing it through a 0.2 μm filter and into a sterile container for subsequent use. The solution was stored at 4° C.

Second, eight mouse tibia bones (1.4-1.6 cm by 3-4 mm diameter) were harvested from four black mice (CD-1) that were 3-4 months old. The four left tibias and four right tibias were placed in 10 ml each of RNALATER™ Solution for approximately 24 hrs at 4° C. After 24 hrs, the bones were divided into half with bone scissors and placed in two beakers containing 10 ml each of decalcification solution prepared as set forth above.

Third, eight tibial halves were ground to powder under liquid nitrogen (the "gold standard" for RNA recovery) while the other corresponding halves were decalcified in the decalcification solution prepared above. After 24 hrs, the four left tibias were removed and rinsed in RNALATER™ Solution for 1 hr and then these were also ground to a powder. The decalcification solution was then changed and after an additional 24 hrs (48 hrs total), the remaining four right tibias were removed, rinsed in RNALATER™ Solution for 1 hr and ground to a powder.

This experimental methodology allowed for a more robust paired-sample t-test statistical analysis (Sig. 2-tailed) of genes common to the extracellular matrix of hard tissues. The analysis results are shown in Table 1. Matrix genes, osteopontin (OPN), osteocalcin (OC), type I collagen (Type I), aggrecan (Agg), bone sialoprotein (BSP) and a reference gene cyclophilin D (Cyc) were examined. No statistical significance ($p > 0.05$) was found between the undecalcified ("Un") samples (RNA removed using "gold standard" freezing and powdering technique) and samples ("Decal") utilizing the decalcification method of the present invention.

TABLE 1

| Paired Samples Test | | | |
|---|---|---|---|
| | | Degrees of Freedom (Df) | Sig. (2-tailed) |
| Pair 1 | OPN Decal - OPN Un | 8 | .140 |
| Pair2 | Cyc Decal - Cyc Un | 7 | .090 |
| Pair 3 | OC Decal - OC Un | 8 | .167 |
| Pair4 | TypeI Decal - TypeI Un | 8 | .126 |
| Pair 5 | Aggrecn De - Agg Undec | 6 | .606 |
| Pair6 | BSP Decal - BSP Undec | 8 | .385 |

Example 5

Decalcification of Human Core Biopsies from Human Proximal Femur, Distal Femur, Proximal Tibia and Fibula First, 10.0 grams of tetrasodium-EDTA was weighed out into a 150 ml sterile beaker and 80 ml of RNALATER™ Solution was added. The pH of the mixture was adjusted to 8-9 and the tetrasodium-EDTA was dissolved with stirring after approximately 30 minutes. The pH was then reduced to 7.6 with a weak acid and RNALATER™ Solution was added to an adjusted final volume to 100 ml. The solution was sterilized by passing it through a 0.2 µm filter and into a sterile container. The solution was stored at 3-4° C. for subsequent use.

Second, core biopsies were obtained surgically from patients who had slipped capital femoral epiphysis (SCFE) and leg length discrepancies. These samples, ranging in diameter from 2-5 mm and length of 1-3 cm, were preserved in RNALATER™ Solution upon removal from the patients. After 24 hrs in RNALATER™ Solution at 4° C., they were decalcified in sterile solution prepared above for 5 days. Initially, one control ("ctrl") sample and one disease-state sample ("slip") were cut in half with a dremmel saw. One half was not placed in the above-described decalcification solution, but instead was ground to a powder in a Spex grinder mill under liquid nitrogen. The other half was placed in the above-described decalcification solution until the hard tissue softened and could be cut with a cryostat knife. Total RNA was isolated according to the TriReagent protocol and reverse transcribed to cDNA. The cDNA was utilized in Experiment 1, below.

Experiment 1

Figure 2:
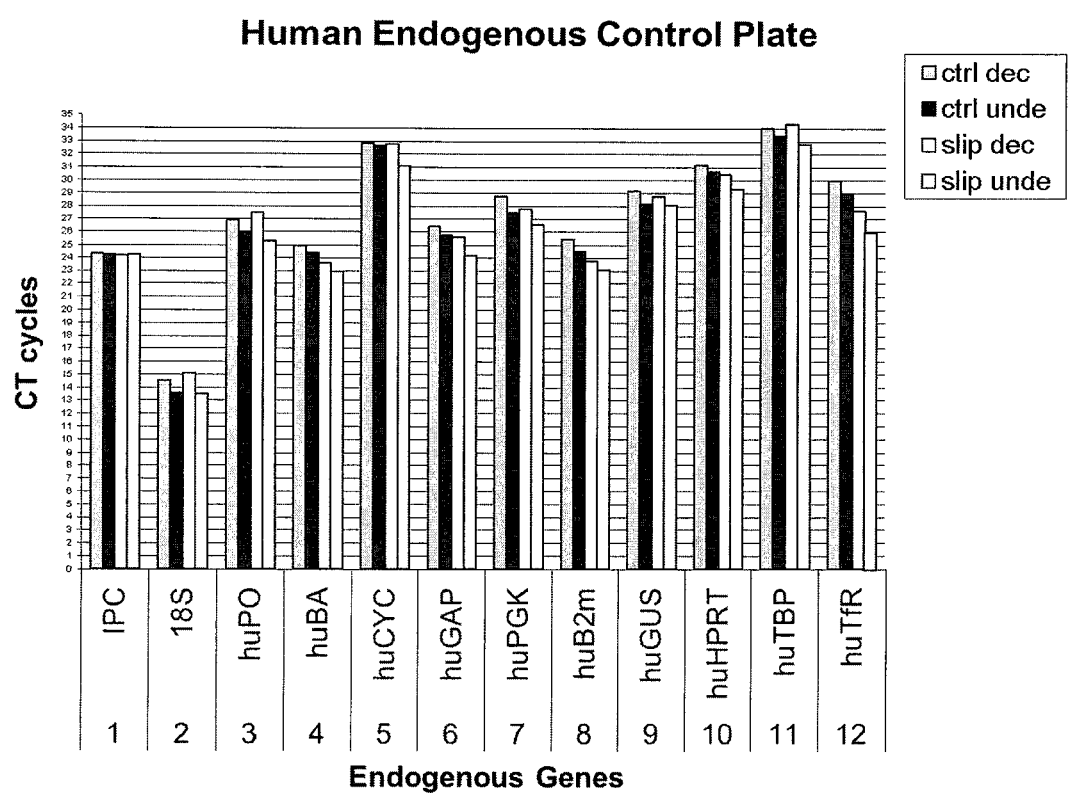
FIG. 2 is a graph reporting the raw data control plate with 11 human reference genes from Applied Biosystems comparing one normal human bone decalcified according to at least one embodiment of the present invention and its undecalcified counterpart and one diseased state ("slip") human bone sample decalcified according to at least one embodiment of the present invention and its undecalcified counterpart. The data show good correlation between sample halves.
Figure 3:
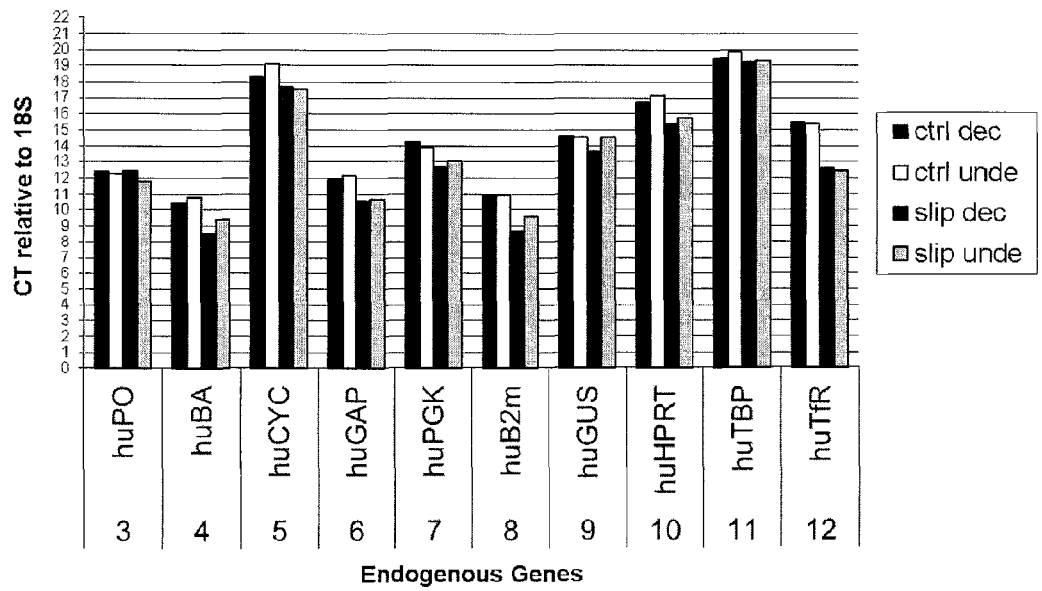
FIG. 3 is a graph reporting the raw data shown in FIG. 2 normalized for the number of cells per sample utilizing 18S rRNA. Little to no variation was noted in gene expression between 2 identical samples (one control tissue bisected) and 2 identical samples (one disease-state tissue bisected) from RNA isolated before and after decalcification according to at least one embodiment of the present invention. A less than 1 Ct difference is considered not statistically significant.

A human endogenous control plate was purchased from Applied Biosystems and a comparison was made between the bisected samples ("ctrl" and "slip") decalcified ("decal") and undecalcified ("unde") halves. These results are represented in FIGS. 2 and 3. FIG. 2 shows the raw data where lane 1 is an internal control and lane 2 represents 18S rRNA which is equivalent to the amount of cDNA loaded into each well. There is a good correlation between the gene expression in the decalcified control sample and its undecalcified counterpart. Also, there were only minor differences in gene expression when the SCFE decalcified sample was compared to its undecalcified counterpart. According to Applied Biosystems protocols, a 1 Ct difference between samples is not considered statistically significant. FIG. 3 normalizes the gene data to 18S rRNA and thus obviates the loading differences or cell numbers between the decalcified and undecalcified counterparts. These data demonstrate a strong correlation for gene expression between the undecalcified sample half and the decalcified half.

Experiment 2

Other human femurs, tibias and fibulas removed during routine orthopedic procedures were placed in RNALATER™ Solution immediately following surgery. Any sample with their length, width and depth dimensions all greater than 5 mm were bisected or reduced by the surgeon to have a thickness of 5 mm for adequate solution infiltration. After 24 hrs in RNALATER™ Solution at 4° C., bone samples were immersed in cold (4° C.) decalcification solution (item 1) in a 10-20×volume to weight. The decalcification solution was changed every approximately 48 hrs and samples were removed when they were judged to be softening from pressure of a forceps. Smaller bones, typically core samples from the tibias and fibulas (0.5-1×0.8-1×0.8-1 cm), were decalcified for 3 days and the larger femurs (0.5-1×1-1.5×1.2-2 cm) were removed after 5 days in the above-described decalcification solution.

Figure 4:
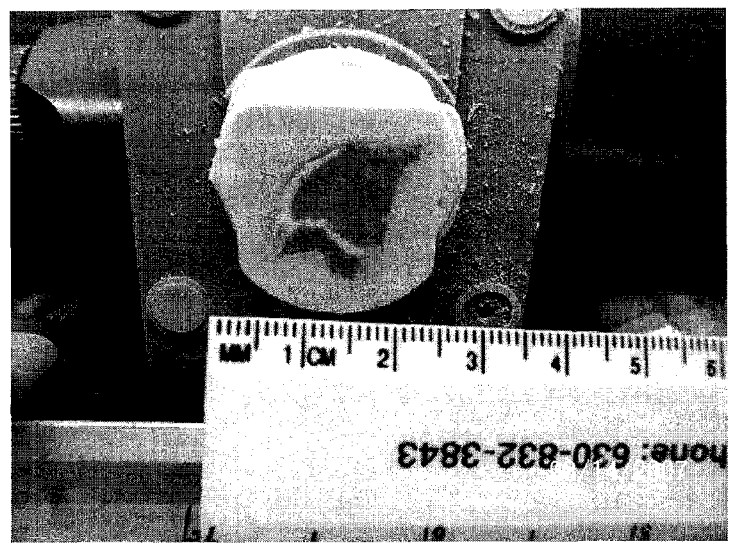
FIG. 4 is a photograph of a tissue sample from a young human proximal femur decalcified according to at least one embodiment of the present invention and embedded in cryo-medium in preparation for being sectioned. The tissue appears intact and complete with red marrow elements, white ribbon of the cartilage growth plate through the center of the bone and the white outer layer which comprises the perichondrium.
Figure 5:
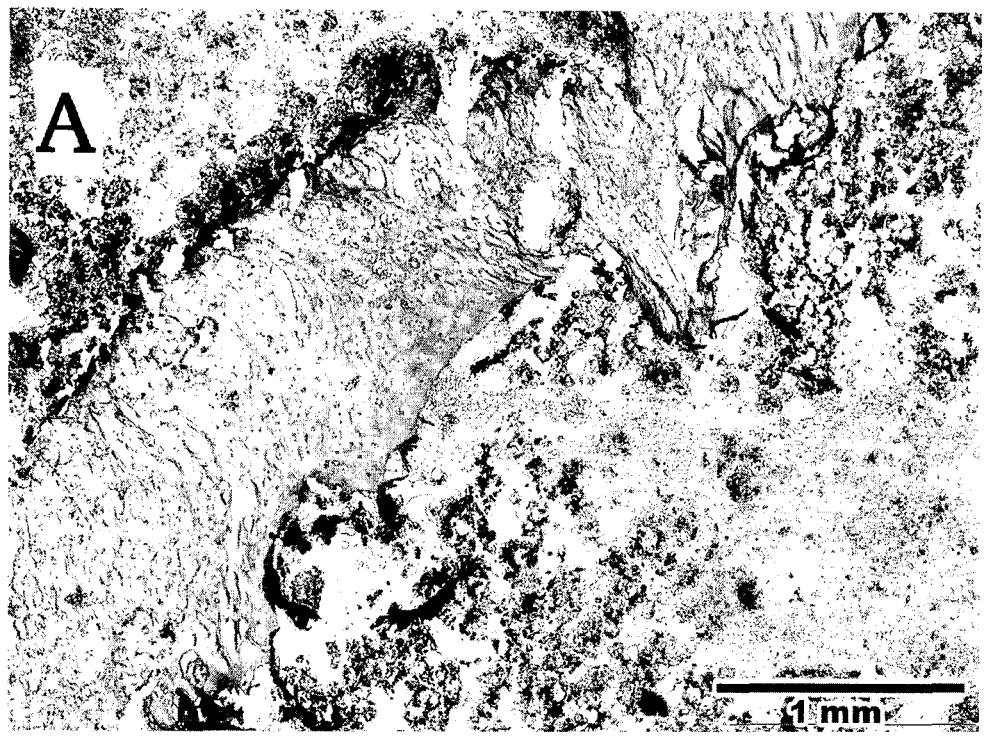
FIG. 5A is an image taken at 4× magnification of sections cut from the human femur shown in FIG. 4 above that has been decalcified according to at least one embodiment of the present invention, cryo-sectioned, stained with eosin and prepared for laser capture microdissection ("LCM") in this example.
FIG. 5B is an image taken at 4× magnification of the stained human femur section shown in FIG. 5A after LCM. The empty area where a group of cells was removed by LCM is designated by a black star.
Figure 5:
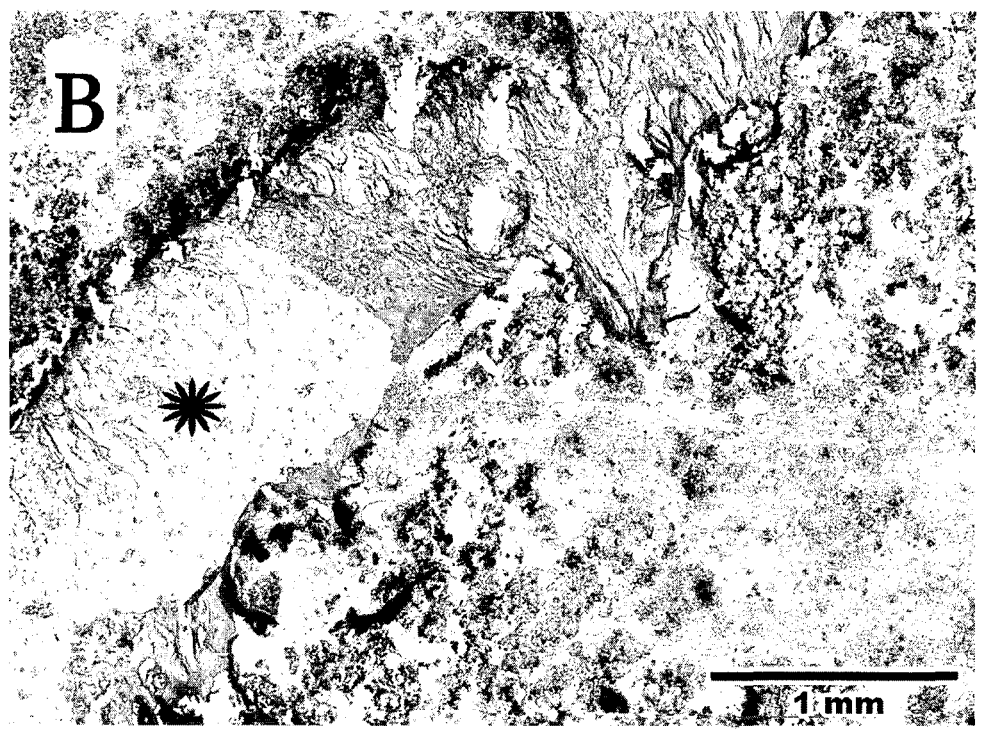
Figure 6:
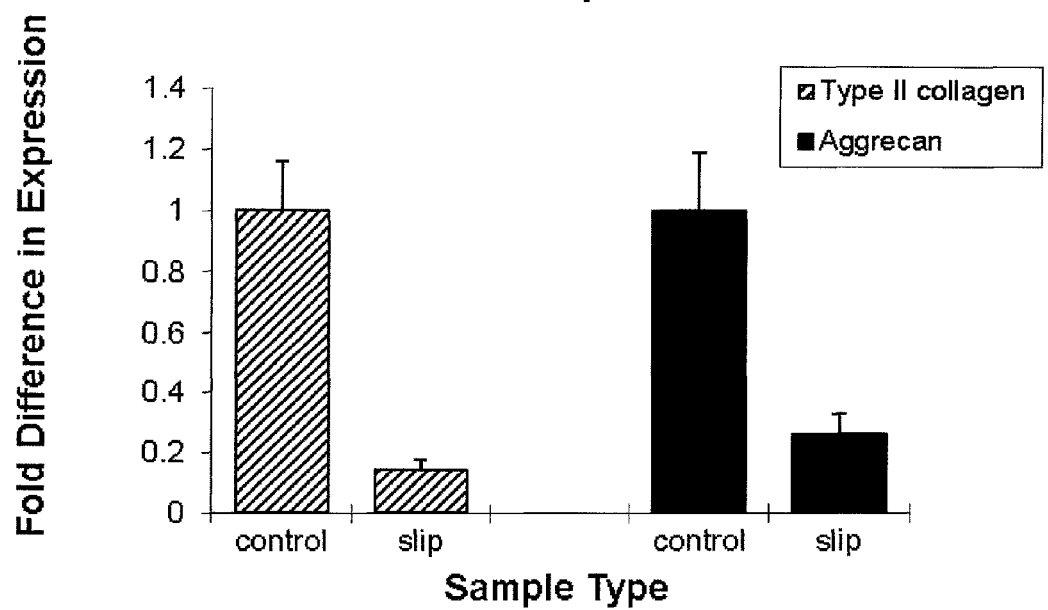
FIG. 6 is a graph reporting the results from the study of growth plate cartilage in normal and SCFE patients shown above in FIGS. 4 and 5. These data showed the statistically significant downregulation of extracellular matrix genes in the human SCFE condition.
Figure 7:
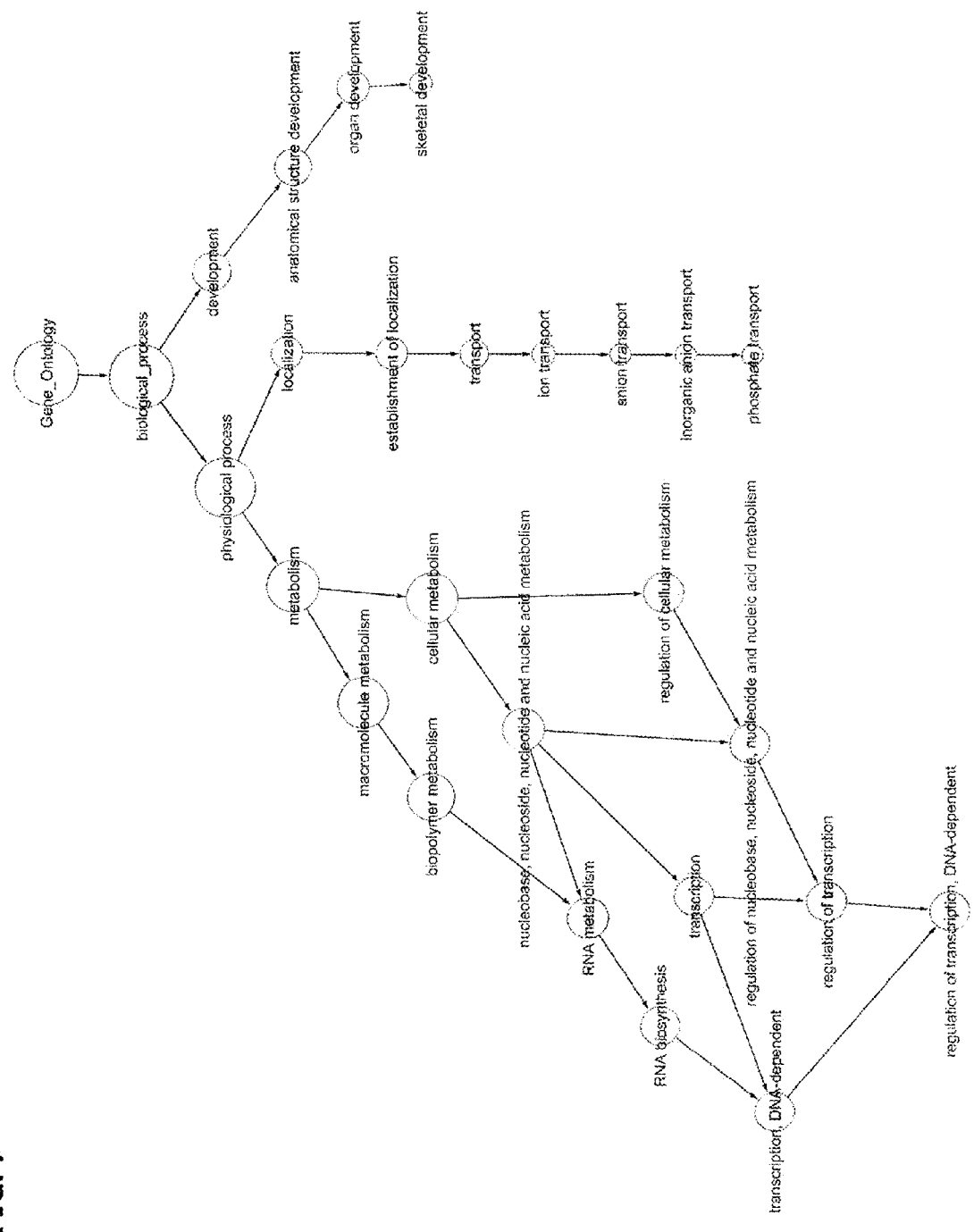
FIG. 7 is a chart showing a microarray analysis of human biopsy samples of control bones compared to SCFE bones utilizing frozen-ground samples. These results confirmed the data presented in FIG. 6 because the grayed-in circles indicate statistical significance in skeletal development where the genes for type II collagen and aggrecan are grouped.

All decalcified samples were in RNALATER™ Solution for approximately 24 hrs at 4° C. to remove decalcification solution. RNALATER™ Solution was briefly washed off with cold RNase-free water for 30 sec and sample was placed in cold tissue embedding medium to prepare for sectioning. The sample morphology appeared preserved with the bone and marrow elements visible and the white cartilage components of the growth plate and perichondrium evident in the example of a proximal femur shown in FIG. 4. The samples were sectioned (4-5 µm) onto clean glass slides, fixed and stained with eosin for laser capture microdissection (FIG. 5A). After LCM (FIG. 5B), cells were lysed, total RNA was isolated and reverse transcribed for qPCR. Results of this study are reported in graphic form in FIG. 6. The downregulation of the extracellular matrix genes of SCFE patients in this study was subsequently confirmed by a microarray analysis utilizing RNA isolated by the standard grinding of control and SCFE samples under liquid nitrogen (FIG. 7). The downregulation of extracellular matrix genes is noted in the grayed area that is labeled as skeletal development. FIG. 7.

Example 6

Mouse Study of Tibial Development with Exercise

First, 10.0 grams of tetrasodium-EDTA was weighed out into a 150 ml sterile beaker and 80 ml of RNALATER™ Solution was added. The pH of the mixture was adjusted to 9 with a base and the tetrasodium-EDTA was dissolved with stirring after approximately 30 minutes. The pH was then reduced to 7.6 with an acid and RNALATER™ Solution was added to an adjusted final volume to 100 ml. The solution was sterilized by passing it through a 0.2 µm filter and into a sterile container. The solution was stored at 3-4° C. for subsequent use.

Figure 8:
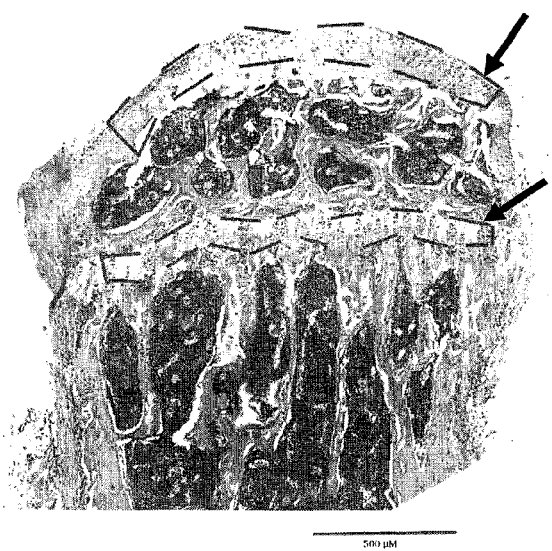
FIG. 8 is an image of a mouse tibia decalcified according to at least one embodiment of the present invention, cryo-sectioned and stained in preparation for laser microdissection. The cell groups identified to be removed by laser cutting are delineated by dashed lines and pointed out by black arrows.
Figure 9:
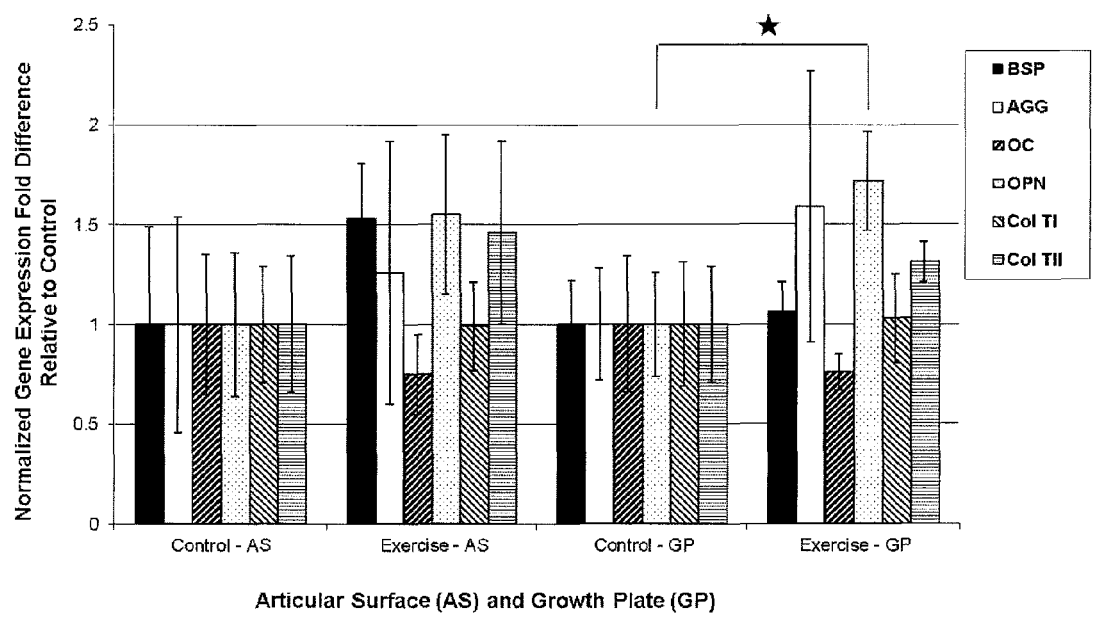
FIG. 9 is a graph reporting the quantitative data generated from microdissection of the specific cell groups in the mouse tibia shown above in FIG. 8.

Eight mice were randomly divided into either cage-control or exercise groups. The exercise group of mice (n=4) were run on a treadmill for several hours per day. At the end of the experiment, the mice were sacrificed and their tibias harvested and preserved in RNALATER™ Solution at 4° C. After 24 hours, tibia bones measuring 1-2 mm by 1.5-2 cm were placed in 15 ml (10-20×) of decalcification solution with stirring for 5 days. The decalcification agent solution was changed every 36-48 hrs. After 5 days of decalcification, the tibia bones were rinsed in RNALATER™ Solution for approximately 24 hrs at 4° C. The RNALATER™ Solution was briefly washed off with cold RNase-free water for 30-60 sec and the sample was placed in cold tissue embedding media to prepare it for sectioning. Each control (n=4) and exercised mouse tibia (n=4) was sectioned 4-5 µm thick in a cryostat with a tungsten carbide blade. Each bone was completely sectioned from the anterior to posterior face comprising over 100 sections per mouse. Two areas of all tibial sections comprising the articular surface (AS) and growth plate (GP) were laser captured and a representative section is illustrated in FIG. 8. The lighter stained areas that are outlined by dashed lines and arrows were the groups of cells to be removed by LCM. These groups of cells, representing two different areas of the mouse bone, were analyzed by isolation of their RNA. Downstream gene expression analysis revealed quality RNA by reference genes 18S rRNA and elongation factor 1 (involved in transcription). A statistical analysis was preformed to detect extracellular matrix gene differences related to exercise. The data is reported in graphic form in FIG. 9.

Example 7

Rabbit Study of Compression on Growth Plate Development

Pins were surgically implanted across the top and bottom of the right and left proximal tibial growth plates of 12 week-old New Zealand white rabbits. On one leg, a compressive device was added to the pins that applied forces of either 10N (n=8) or 30N (n=8) (experimental samples) for either 2- or 6-weeks. The contralateral leg served as a sham control (n=16). The rabbits were sacrificed at the appropriate time point and tibial bones were harvested, bisected and placed in RNALATER™ Solution for approximately 24 hrs. Gene studies in this experiment were accomplished by grinding bisected halves under liquid nitrogen to a powder and then isolating the RNA.

20.0 grams of tetrasodium-EDTA was weighed out into a 250 ml sterile beaker and 160 ml of RNALATER™ Solution was added. The pH of the mixture was adjusted to 9.5 with a basic solution (NaOH) and the tetrasodium-EDTA was dissolved with stirring after approximately 45 minutes. The pH was then reduced to 7.6 with an acid and RNALATER™ Solution was added to an adjusted final volume to 200 ml. The solution was sterilized by passing it through a 0.2 µm filter and into a sterile container. The solution was stored at 3-4° C. for subsequent use.

One bisected sample (approx. 0.5×1×2 cm) from each group (2 wk control and experimentals and 6 wk control and experimentals) was decalcified separately (n=6 bones) using a decalcification agent solution of 15 ml each. The solution was changed once on day 2 and softened bones were removed after 4 days and rinsed in RNALATER™ Solution to remove decalcification solution for approximately 24 hrs at 4° C. The RNALATER™ Solution was briefly washed off with cold RNase-free water for 30-60 sec and the sample was placed in cold tissue embedding media to prepare for sectioning. Each control (n=2) and experimental rabbit bone (n=4) was sectioned 4-5 µm thick in a cryostat with a tungsten carbide blade. Growth plate chondrocytes from tibial bones of the rabbits were laser captured by microdissection and gene expression analysis was compared the same analysis from bones that were ground to a powder.

Example 8

Pig Study of Hypothyroidism on Proximal Femur Development

Four miniature swine were divided into two groups and one group (n=2) was given a drug to decrease their thyroid function. After 14 weeks, the pigs were sacrificed and the proximal and distal femurs and the proximal tibias were harvested. Surgeons bisected the pig bones and then placed them in RNALATER™ Solution for approximately 24 hrs at 4° C. After one day, the samples were snap-frozen and stored at minus 80° C. until analysis.

20.0 grams of tetrasodium-EDTA was weighed out into a 250 ml sterile beaker and 160 ml of RNALATER™ Solution was added. The pH of the mixture was adjusted to 9.5 with a basic solution (NaOH) and the tetrasodium-EDTA was dissolved with stirring after approximately 45 minutes. The pH was then reduced to 7.6 with an acid and RNALATER™ Solution was added to an adjusted final volume to 200 ml. The solution was sterilized by passing it through a 0.2 µm filter and into a sterile container. The solution was stored at 3-4° C. for subsequent use.

Figure 10:
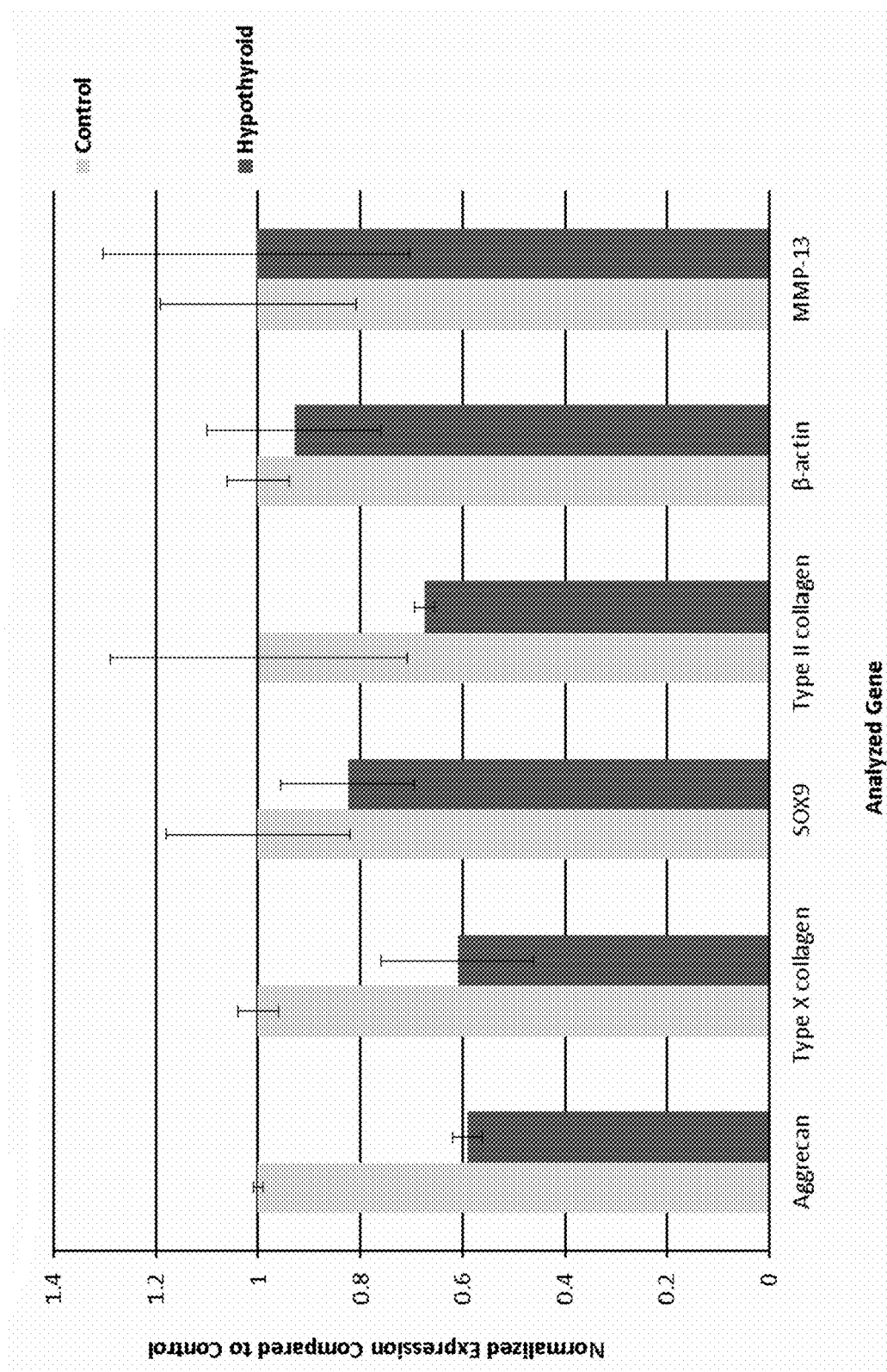
FIG. 10 is graph reporting the quantitative data generated from microdissection of pig normal and hypothyroid proximal femur growth plates after being decalcified according to at least one embodiment of the present invention.

The pig bones used had varying dimensions of 0.3-0.5×1-2.5×2-3.0 cm. First, the four proximal femurs (size approx. 0.5×2.5×1.7 cm) were separately decalcified in 20 ml each of decalcification solution after removal from minus 80° C. storage. The four proximal femurs were demineralized for 5 days at 4° C. with the solution changed on days 2 and 4. The softened pig proximal femurs were rinsed in RNALATER™ Solution for approximately 24 hrs at 4° C. The RNALATER™ Solution was briefly washed off with cold RNase-free water for 30-60 sec and the sample was placed in cold tissue embedding media to prepare for sectioning. Each control (n=2) and hypothyroid (n=2) bone was sectioned 4-5 µm thick in a cryostat with a tungsten carbide blade. RNA was isolated from laser captured growth plate cartilage and gene expression compared by RT-qPCR. Results were highly correlated between sample types resulting in a statistical significance by student's t-test for n of 2 in FIG. 10.

The following decalcification solution was used with the four proximal tibias and four distal femurs. 40.0 grams of tetrasodium-EDTA was weighed out into a 500 ml sterile beaker and 350 ml of RNALATER™ Solution was added. The pH of the mixture was adjusted to 9.5 with a basic solution (NaOH) and the tetrasodium-EDTA was dissolved with stirring after approximately 45 minutes. The pH was then reduced to 7.6 with an acid and RNALATER™ Solution was added to an adjusted final volume to 400 ml. The solution was sterilized by passing it through a 0.2 µm filter and into a sterile container. The solution was stored at 3-4° C. for subsequent use.

Subsequently, the four proximal tibias (approx. 0.5×0.9×1.4 cm) and four distal femurs (approx. 0.5×0.8×3 cm) were removed from minus 80° C. storage and placed in separate beakers containing 20 ml of cold decalcification solution for each bone. The solution was changed after 48 hrs and the softened bones were removed after 4 days to RNALATER™ Solution to remove decalcification solution for approximately 24 hrs at 4° C.

Figure 11:
FIG. 11A is an image taken at 4× magnification of a representative section cut from a pig proximal tibia that has been decalcified according to at least one embodiment of the present invention, cryo-sectioned onto PEN membrane slides, stained with eosin and prepared for laser capture microdissection ("LCM") in this example.
FIG. 11B is an image taken at 4× magnification of the stained pig proximal tibia section shown in FIG. 11A after LCM. The empty area is where a group of cells was removed by LCM.
FIGS. 11C and 11D are images taken at 4× of captured growth plate chondrocytes from pig proximal tibia sections. From these cells, RNA will be isolated and used in RT-qPCR analyses.
Figure 11:
Figure 11:
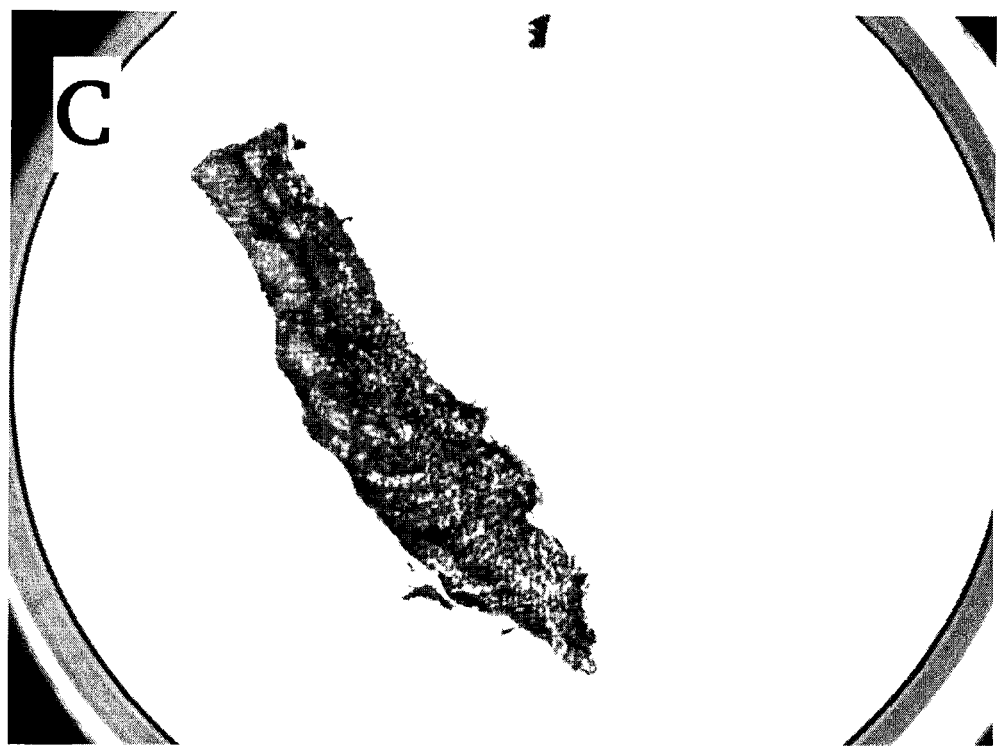
Figure 11:
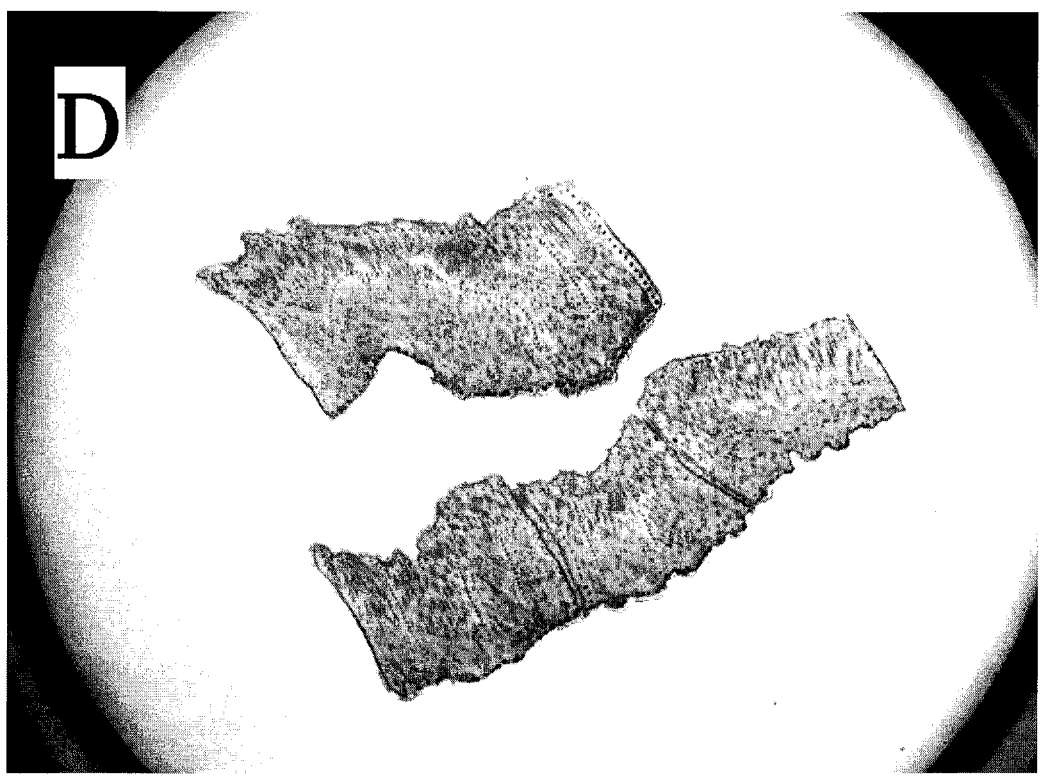

The RNALATER™ Solution was briefly washed off with cold RNase-free water for 30-60 sec and the sample was placed in cold tissue embedding media to prepare for sectioning. Each control (n=2) and hypothyroid (n=2) bone was sectioned 15-20 µm thick in a cryostat with a tungsten carbide blade onto new plastic (PEN) membrane slides. These new slides although difficult to use allow for more cells to be isolated in a shorter time frame. This invention made it a possibility to use an antiroll plate device in the cryosectioning art for section transfer to the PEN membrane slides. An example of the section on the slide is shown in FIG. 11. FIG. 11A is the view under the laser capture microscope of the stained and prepared section. FIG. 11B is the section after removal of cells and in FIGS. 11C and 11D are representative caps showing the captured isolated cell groups. RNA was then isolated from laser captured growth plate cartilage of these pig bones and gene expression comparisons by RT-qPCR of control and hypothyroid animals is ongoing.

What is claimed is:
1. A method of preparing a decalcification agent solution for the decalcification of hard without chemical fixation and without degrading the ribonucleic acids (RNA) contained therein, comprising:

A. providing an RNA preservation solution;
B. adding a decalcification agent to said RNA preservation solution; wherein said decalcification agent comprises tetrasodium-ethylenediaminetetra-acetic acid (tetrasodium-EDTA) the concentration of said decalcification agent in said RNA preservation solution is from 9 g per 90 ml to 10 g per 90 ml;
C. adjusting the pH of the mixture of Step B to a pH of from about 8 to about 10 and stirring until the decalcification agent is substantially dissolved;
D. adjusting the pH of the mixture of Step C to a pH of from about 7.4 to about 7.7; and
E. sterilizing and collecting the mixture of Step D in a sterilized container.

2. The method of claim 1 wherein the mixture of Step C is stirred for from about 30 minutes to about 60 minutes.

3. The method of claim 1 wherein the pH of the mixture of Step C is adjusted to a pH of about 7.6.

4. The method of claim 1 wherein the mixture of Step E is sterilized by filtration.

5. The method of claim 4 wherein the mixture of Step E is sterilized using a 0.2 µm filter.

* * * * *